United States Patent
Viladot Perice et al.

[11] Patent Number: 6,136,032
[45] Date of Patent: Oct. 24, 2000

[54] IMPLANT FOR CORRECTING FLAT FOOT CONDITION

[75] Inventors: Ramon Viladot Perice, Barcelona, Spain; Greta Dereymaeker, Oud-Heverlee, Belgium; Patrice Diebold, Nancy, France; Beat Hintermann, Riehen, Switzerland

[73] Assignee: European Foot Platform, Nancy, France

[21] Appl. No.: 09/390,995

[22] Filed: Sep. 7, 1999

[30] Foreign Application Priority Data

Sep. 4, 1998 [FR] France ................................. 98 11107

[51] Int. Cl.⁷ ...................................................... A61F 2/42
[52] U.S. Cl. ..................................... 623/21.18; 623/21.11
[58] Field of Search ............................ 623/21.18, 21.11, 623/13.14, 21.12, 23.47, 23.5; 606/53

[56] References Cited

U.S. PATENT DOCUMENTS

| 4,450,591 | 5/1984 | Rappaport ............................. 623/21.11 |
| 5,531,792 | 7/1996 | Huene ................................... 623/23.47 |
| 5,957,953 | 9/1999 | DiPoto et al. ........................... 606/232 |

FOREIGN PATENT DOCUMENTS

| 560 249 | 9/1993 | European Pat. Off. . |
| 2 543 821 | 10/1984 | France . |
| 2645735 | 10/1990 | France ..................................... 623/21 |
| 2653660 | 3/1991 | France . |
| 97/29693 | 8/1997 | WIPO . |

*Primary Examiner*—Paul J. Hirsch
*Attorney, Agent, or Firm*—Pillsbury Madison & Sutro

[57] ABSTRACT

A surgical device implantable in the subtalar tunnel for treating the flat foot condition, composed of: a central cylindrical body having an outer cylindrical surface provided with a first screw thread; an expansion cone having a longitudinally extending internal bore provided with a second screw thread mateable with the first screw thread, the cone further having an external surface of conical form; and an external cylinder having an internal conical surface engageable with the cone and constructed to be radially expandable in response to movement of the cone in a longitudinal direction relative to the cylinder, the cone being longitudinally moveable by rotation relative to the cylindrical body while the first and second threads are in threaded engagement with one another.

16 Claims, 5 Drawing Sheets

IMPLANT FOR CORRECTING FLAT FOOT CONDITION

BACKGROUND OF THE INVENTION

The present invention concerns an implant device for correcting an abnormal condition known as flat foot (Talipes planus), and particularly an expanding implant device to reshape the natural arch of a foot having that condition.

In order to remedy this condition in a child, which is due to the loss of normal anatomic connections of the talus and the calcaneus, it has recently been suggested to introduce a prosthetic device into the subtalar tunnel between the talus and the calcaneus. However, this introduction of such a prosthetic material presents the problem of maintaining the material in the subtalar tunnel, which anatomically has the form of a funnel which opens laterally, i.e., toward the outside. Thus, it is known to implant a screw to provide a temporary talus-calcaneus gliding joint restoring to the various parts their normal anatomical relationships and which brings into play the restructuring action associated with the growth of the child. The growth erases the dysplasia and restores the cohesion of the whole. Maintenance is achieved by a trans-talus-calcaneus screw and once the restructuring is achieved, the temporary attachment is removed, freeing the subtalus pair.

Around 1975 it was proposed to utilize a silicone prosthesis having a generally frustoconic form and which has an appendage. The overall arrangement is very close in form to a wine glass. Its geometry permits it to be very congruent with the space in which it must be implanted. Thus, its form permits this prosthesis to be perfectly adapted in that space.

The drawbacks of such a prosthesis are linked on the one hand to the silicon material whose behavior in response to mechanical forces is not completely known and on the other hand to the associated surgical technique. In effect, in order to introduce this implant, the physician must make a double incision, one on the medial face and the other on the lateral face of the foot.

In order to eliminate these drawbacks, there has been created another device whose implantation requires only a single incision. This endo-orthesis is made of a high density polyethylene and has the form of a cylinder having a rim at its base. It has a funnel-shaped opening along its longitudinal axis and a screw is introduced into this opening. The cylinder is cut over the interior ⅔ of its length into four quarters intended to be expanded under the effect of the advance of the screw along the axis of the cylinder. The endo-orthesis is threaded interiorly. This device has for its function to open the subtalar tunnel in order to reposition the talus relative to the calcaneus. The major drawback of this implant is that its expanded form is not absolutely congruent with the subtalar tunnel cavity, even after insertion of the internal screw into the axial passage.

BRIEF SUMMARY OF THE INVENTION

A primary object of the invention is to overcome the above-mentioned drawback, as well as other drawbacks.

One specific object of the invention is to provide an implant for correcting the flat foot condition which is expandable and which requires only a single incision.

Another specific object of the invention is to provide an implant for the treatment of flat foot which is congruent with the subtalar tunnel.

Another object of the invention is to provide an implant for flat foot which is expandable in a diametrically uniform manner.

Yet another object of the invention is to provide an implant for flat foot which can be correctly housed in the subtalar tunnel, while being easily locked in place.

The above and other objects according to the invention are achieved by the provision of a surgical device composed of three basic parts:

a central cylindrical body having an outer cylindrical surface provided with a first screw thread, said cylindrical body having a head;

an expansion cone having a longitudinally extending internal bore provided with a second screw thread mateable with the first screw thread, said cone further having an external surface of conical form; and an external cylinder having an internal conical surface engageable with said cone and constructed to be radially expandable in response to movement of said cone in a longitudinal direction relative to said cylinder, said cone being longitudinally moveable by rotation relative to said cylindrical body while said first and second threads are in threaded engagement with one another.

According to preferred embodiments of the invention, the external cylinder is constituted by a biocompatible and/or biodegradable deformable material, for example, of polyethylene, or a metal.

The central body and the expansion cone may each be of a metal material, for example, titanium or stainless steel.

However, it is to be understood that each part of the device according to the invention may be made of any suitable biocompatible material having the requisite mechanical properties, including the requisite deformability in the case of the external cylinder and the requisite mechanical strength and resistance to deformation in the case of the central body and the expansion cone. Suitable materials that may be selected will be readily apparent to those skilled in the art to which this invention relates.

As the central body is screwed into the expansion cone, the expansion cone acts to expand the diameter of the external cylinder by an amount between 0.5 mm and 2 mm along its entire length and in a manner that is uniform around the diameter of the device, and particularly around the diameter of the external cylinder According to preferred embodiments of the invention, the external cylinder is provided with notches in its external surface and in its internal surface. The sum of the depth of a notch in the external surface and of a notch in the internal surface is preferably greater than the thickness of the external cylinder and the notches in the external surface are angularly offset from the notches in the internal surface. With this arrangement, the external cylinder is capable of expanding uniformly in a manner that increases its outer diameter. All of the notches extend over the entire length, or axial dimension, of the external cylinder.

The external cylinder is further provided with means for preventing withdrawal, or retraction, of the device. For example, these means are constituted by substantially annular fins that extend at a median angle of between 20° and 80° with respect to the longitudinal axis of the device. Preferably, the median angle is of the order of 45°. The fins preferably have a height of the order of 1–2 mm. However, the height may be varied from this value to assure secure locking. Fins having this form of construction permit an effective blockage, or locking, of the device in the subtalar tunnel.

The external surface of the central body is threaded in one direction. For example, the central body may have a lefthand thread. In addition, the central body is machined at its distal end, which is the end that will be trailing as the device is inserted, to provide a feature that permits the engagement by an instrument for rotating the central body.

The expansion cone has a smooth external face which is conical, while the external cylinder has a smooth internal face which is also conical. The cone angle defined by the outer face of the expansion cone is identical to that of the internal face of the external cylinder. The expansion cone has an internal surface which is threaded in one direction over a proximal part. For example, this will be constituted by a lefthand thread when the central body is provided with a left-hand thread. The internal surface may then have a right-hand thread over a distal part. In addition, the expansion cone is machined to have a feature, such as a slot, which permits the introduction of another instrument that can act to prevent rotation of the expansion cone so that the expansion cone can be displaced in translation along the longitudinal axis of the device and relative to the external cylinder in response to rotation of the central body.

There will be presented below a more detailed description of an exemplary, non-limiting embodiment of the invention, presented with reference to the attached drawings, will permit a better understanding of the invention and its novel features and advantages.

DETAILED DESCRIPTION OF THE INVENTION

Figure 2:
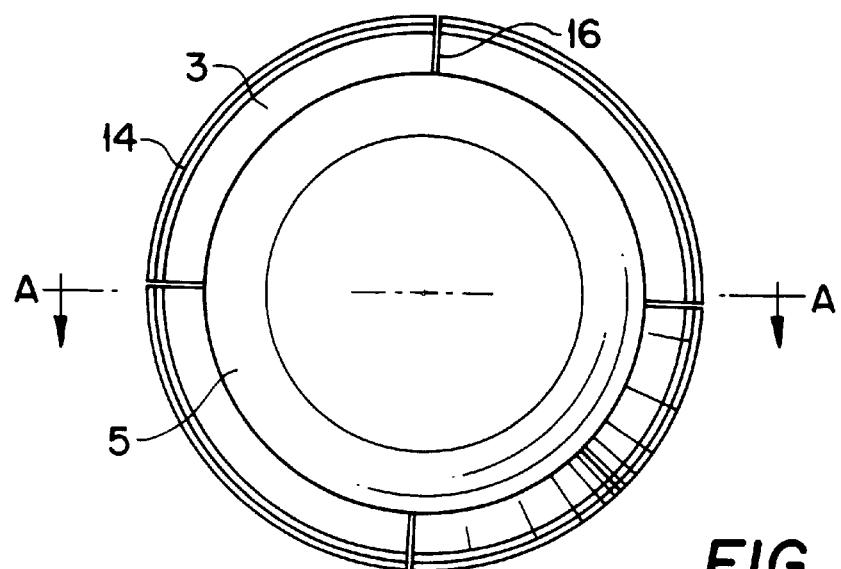
FIG. 2 is an end view of the illustrated embodiment, viewed from the bottom of FIG. 1.

FIGS. 1–6 illustrate a preferred embodiment of a surgically implantable device according to the invention for correcting a flat foot condition. The device is shown in a state of initial assembly in FIGS. 1 and 2, this being the state before the device is installed in a tarsal sinus cavity.

The device according to the invention is composed of three elements: a central body 1, an expansion cone 2 and an external cylinder 3.

Central body 1 has the general form of a screw composed of a cylindrical shank 4 which is coaxial with the longitudinal axis of the device, a relatively large head 5 and a shoulder 6 interposed between shank 4 and head 5. Shoulder 6 has a diameter which is larger than that of shank 4 and smaller than that of head 5.

Central body 1 and cone 2 are preferably made of a metal, for example, titanium or stainless steel and has a substantial length, for example of the order 10 to 20 mm. The purpose of head 5 is to prevent displacement of central body 1 along the longitudinal axis, upwardly with respect to the orientation of FIG. 1, toward the right with respect to external cylinder 3.

When the device according to the invention is introduced into the subtalar tunnel, it is oriented so that head 5 comes to abut against the base of the tunnel, which is then end of the tunnel closest to the medial side of the foot. Head 5 will be identified as constituting the proximal extremity of the device since it is the extremity that will be closest to the base of the tunnel.

The external surface of shank 4 is provided along its entire length with a screw thread 7 which is, for example, a left-hand thread. Shank 4 is provided at the axial extremity opposite to head 5, or the distal extremity, with a shaped part, or feature, 8 that permits engagement of an instrument for rotating body 1. Feature 8 is preferably in the form of a slot, as shown in the drawings, which can be operatively engaged by a screwdriver tip.

Expansion cone 2 has the general form of a conic frustum coaxial width the longitudinal axis of the device and has a length somewhat greater the length of shank 4. The smaller diameter end of cone 2 faces toward the proximal extremity of the device, while the larger diameter end is at the distal extremity of the device.

Expansion cone 2 is formed to have a cylindrical passage which is coaxial with the longitudinal axis of the device and extends throughout the entire length of cone 2. This cylindrical passage has an internal diameter substantially equal to the external diameter of shank 4 and is provided with a first internal screw thread 9 at the side of the proximal extremity of the device, i.e., the extremity closer to head 5, and a second internal screw thread 10 at the distal extremity of cone 2, i.e., the extremity remote from head 5. First screw thread 9 cooperates with screw thread 7 of shank 4 and thus has the same thread direction and pitch as thread 7. In contrast, second thread 10 has a thread direction opposite to that of first thread 9.

First thread 9 preferably extends along more than ¾ of the length of cone 2, while second thread 10 extends over the remaining length of cone 2, with possibly a groove interposed between threads 9 and 10, as shown. Second thread 10 is intended to receive a grasping instrument. It is, however, possible to provide, instead, a shaped part different from a screw thread to receive a grasping instrument.

Figure 4:
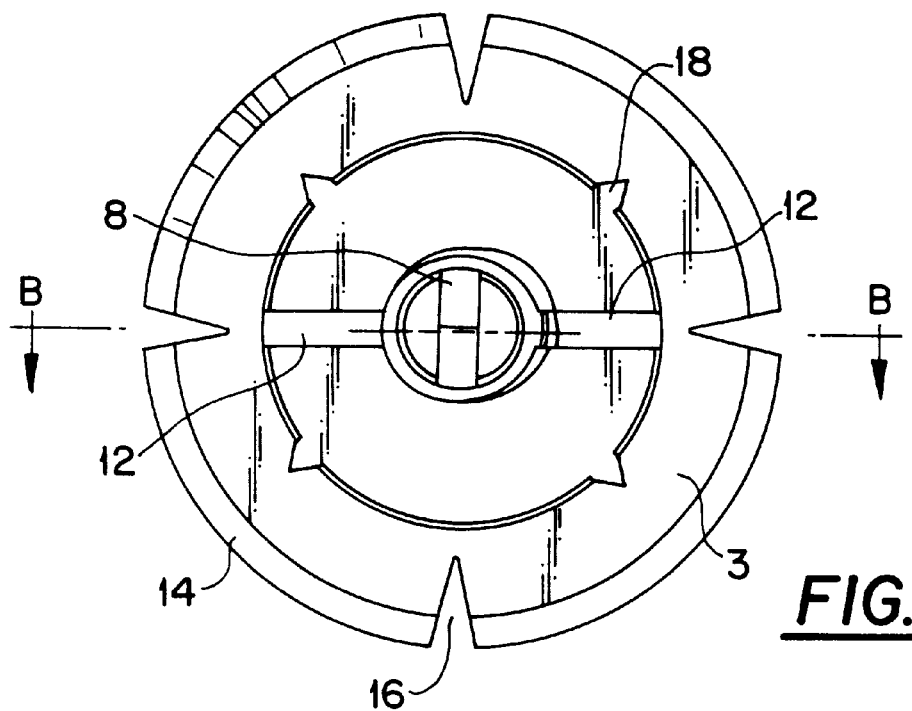
FIGS. 3 and 4 are views similar to those of FIGS. 1 and 2, FIG. 3 being a cross-sectional view along line B—B of FIG. 4, showing the device in the state in which the external cylinder is radially expanded to its full extent.

At its large diameter end, expansion cone 2 comprises in addition, on a face 11 perpendicular to the longitudinal axis of the device, a zone provided with another feature, such as two slots 12 shown in FIG. 4, for engagement by an instrument for blocking rotation of cone 2, and thus also blocking rotation of external cylinder 3.

The external lateral surface of cone 2 is completely smooth, in a manner to be able to slide longitudinally with respect to external cylinder 3. For the same reason, the internal surface of cylinder 3 is also perfectly smooth.

External cylinder 3 has a generally frustoconical form and is preferably made of polyethylene and/or bioresorbable material, bioresorbable matter being preferred. Cylinder 3 is formed to have an internal, longitudinally extending cavity 13 which is bounded by the above-mentioned smooth internal surface of cylinder 3 and in which cone 2 engages.

The external surface of cylinder 3 is provided with one or more generally cylindrical fins 14 which are shaped and oriented to oppose withdrawal of the device after it has been implanted.

In addition, cylinder 3 is provided with a plurality of notches, or slits, including slits 16 cut into the external surface of cylinder 3 and notches, or slits, 18 cut into the internal surface of cylinder 3. Preferably, there are at least 3 slits formed in each surface, the slits in each surface being spaced regularly from one another around the circumference of cylinder 3. More preferably, there are at least four slits cut into each surface of cylinder 3.

Slits 16 are angularly offset from slits 18, as shown in FIG. 4, with each slit 18 being equispaced from two successive slits 16. With this arrangement, as can be seen in FIG. 4, when cone 2 is advanced longitudinally into the space enclosed by cylinder 3, cylinder 3 is expanded radially, which expansion is made possible, and accompanied, by a circumferential spreading, or opening, of slits 16 and 18.

Figure 1:
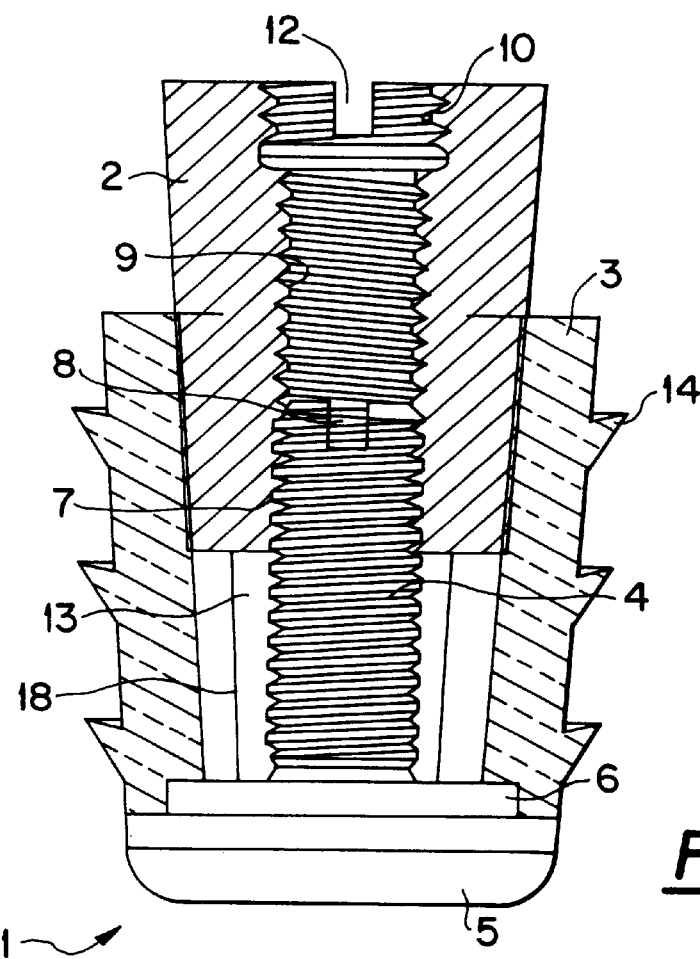
FIG. 1 is a cross-sectional view, along line A—A of FIG. 2, of a preferred embodiment of the invention, in a state prior to radial expansion of the external cylinder.
Figure 5:
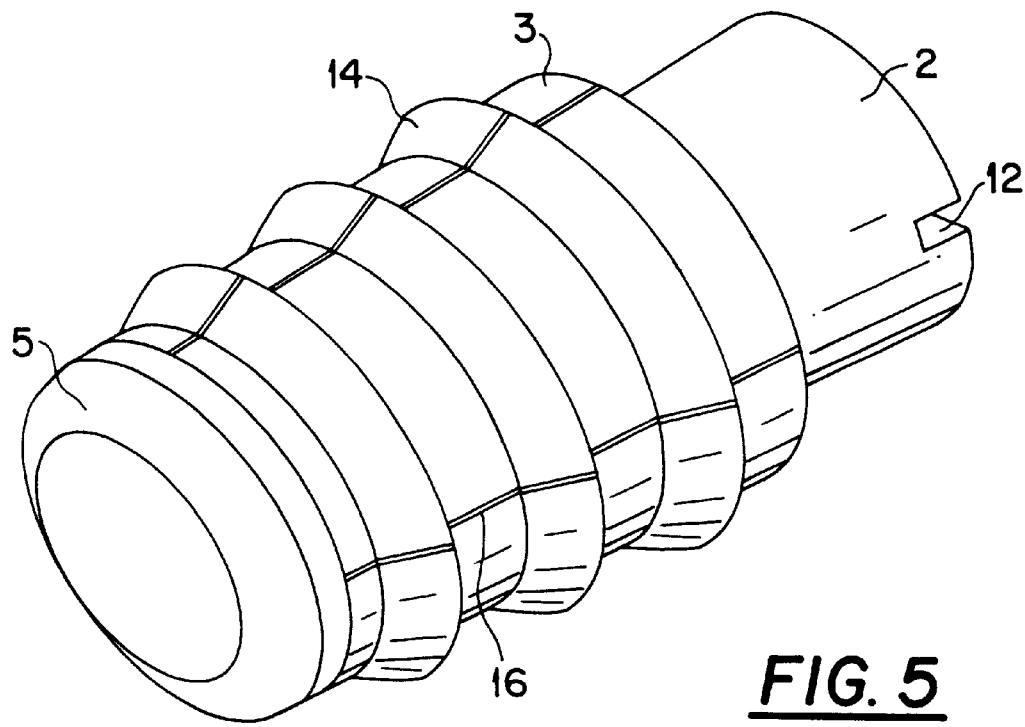
FIGS. 5 and 6 are, respectively, a proximal end perspective view and a distal end perspective view showing the components of the illustrated embodiment in the state illustrated in FIGS. 1 and 2.
Figure 6:
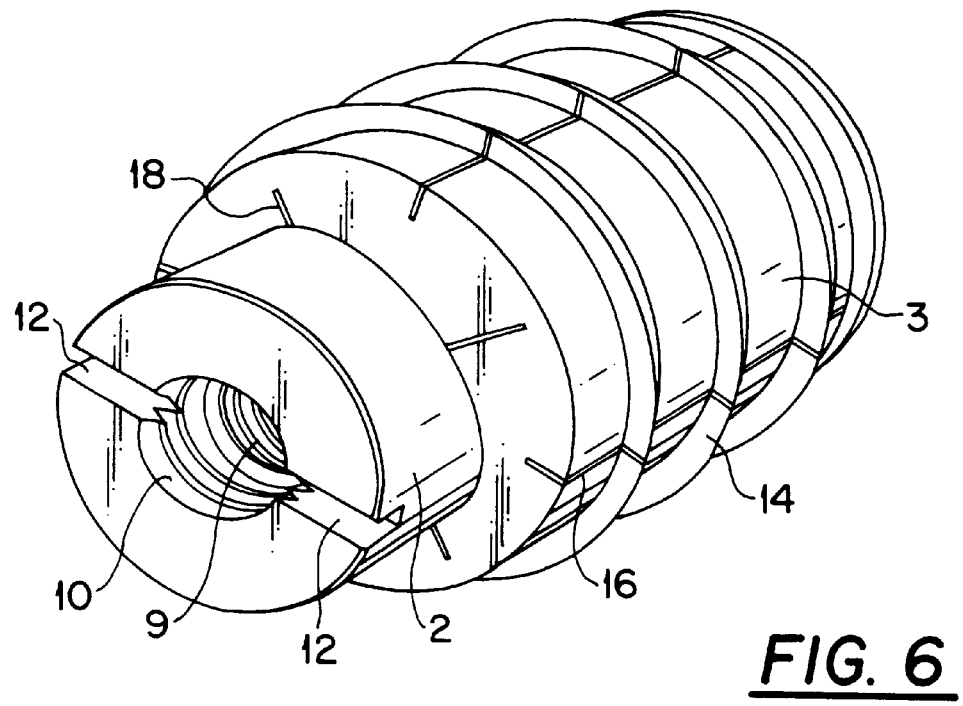

FIG. 5 is a proximal end perspective view and FIG. 6 is a distal end perspective view of the implant device according to the invention in the state shown in FIGS. 1 and 2.

Figure 7:
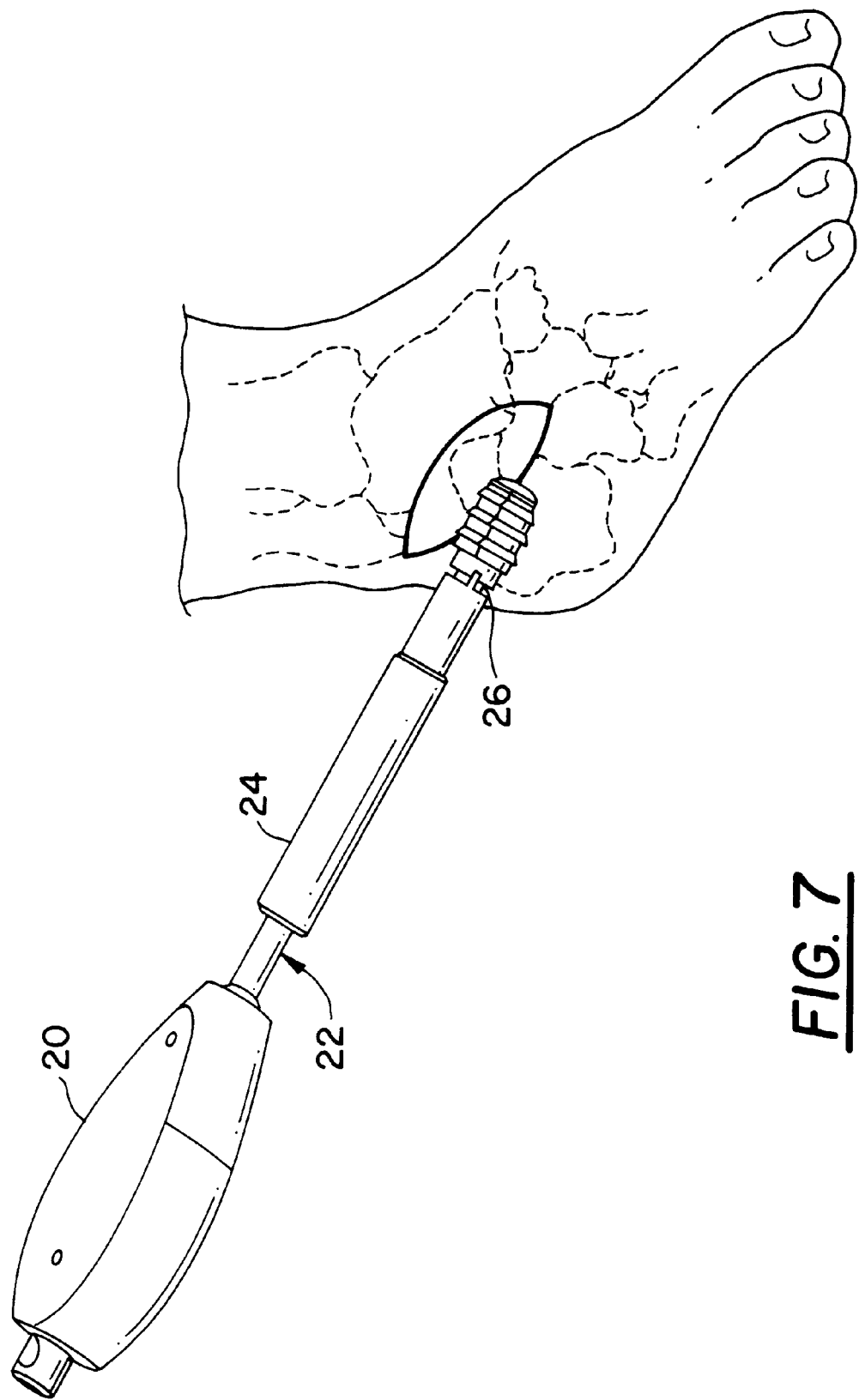
FIGS. 7 and 8 are perspective views showing two tools for implanting the device.

FIG. 7 is a perspective view showing a first exemplary tool which can be employed for implanting a device according to the invention. The tool includes a casing 20 that carries an elongated shaft 22. Shaft 22 is provided at its free end with a male screw thread (not visible) for engaging in thread 10 in cone 2. Shaft 22 is surrounded by a sleeve 24 that is formed to provide, at its end remote from casing 20, two laterally diametrically opposed screwdriver tips 26 each for engaging a respective one of slots 12.

Figure 8:
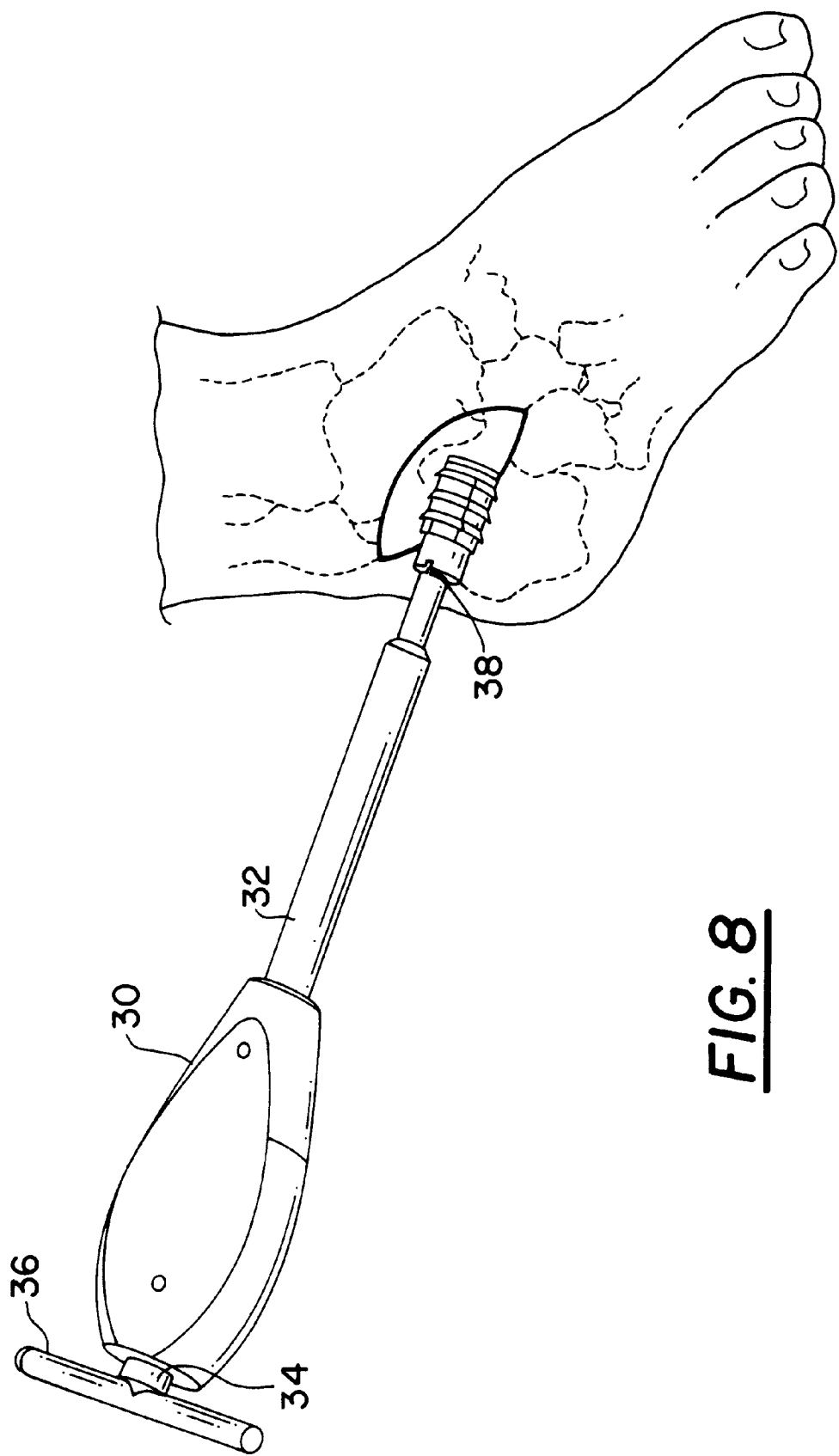

FIG. 8 is a view similar to that of FIG. 7 showing a second exemplary tool which can be employed for the implanting procedure. This tool includes a casing 30 that carries an elongated hollow sleeve 32. Sleeve 32 is provided at its free end, remote from casing 30, with two laterally diametrically opposed screwdriver tips 38 each for engaging a respective one of slots 12. A shaft 34 extends through casing 30, and sleeve 32 and is provided at its rear end with a handle 36 via which shaft 34 can be rotated relative to casing 30. Shaft 34 is formed to provide, at its end remote from casing 30, a screwdriver tip (not visible) for engaging in slot 8.

Implantation of the device is effected in the following manner.

A single incision is made in the foot at the lateral side of the subtalar tunnel and the implant device is provided in the state shown in FIGS. 1, 2, 5 and 6. The male thread on shaft 22 of the tool shown in FIG. 7 is screwed into thread 10. Screwdriver tips 26 at the end of sleeve 24 are introduced into slots 12. The implant device is then introduced into the subtalar tunnel and placed in the desired position. Then, shaft 22 is unscrewed from cone 2 and the tool is withdrawn.

Then the tool shown in FIG. 8 is manipulated to insert the screwdriver tip on shaft 34 into engagement with slot 8 and to insert screwdriver tips 26 into engagement with slots 12. During this operation, the implant device is located within the subtalar tunnel, although this position is not shown in FIG. 8. Shaft 34 is then rotated with the aid of handle 36 while casing 30 is gripped by the physician in order to hold sleeve 32 and screwdriver tips 38 stationary. Thus, central body 1 is rotated while cone 2 is prevented from rotating.

Figure 3:
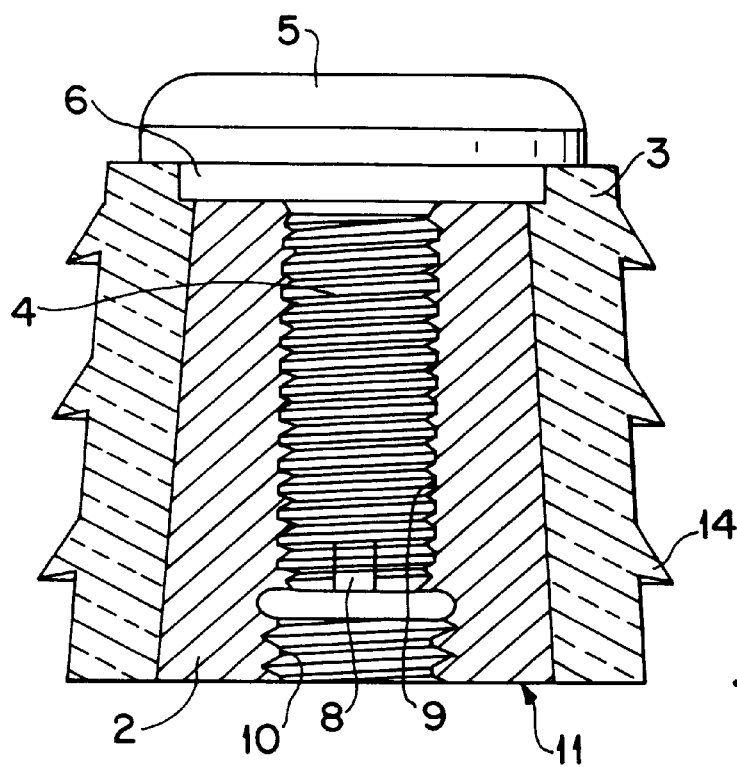

As body 1 is rotated, the engagement between threads 7 and 9 causes cone 2 to be displaced axially relative to cylinder 3 toward head 5 so that cone 2 penetrates into the space enclosed by cylinder 3 while radially expanding cylinder 3. The final position of cone 2 relative to shaft 3 is shown in FIGS. 3 and 4. In this state, slits 16 and 18 have spread while cylinder 3 has expanded radially. As a result, fins 14 come to engage the walls of the subtalar tunnel so that the implant device is locked in position in the tunnel. Then the tool is withdrawn and the incision is closed.

Thus, the device according to the invention has the advantage of requiring only a single incision and of having a geometry which permits it to mate in an optimum manner in the subtalar tunnel.

This application relates to subject matter disclosed in France, Application number FR98 11107, filed on Sep. 4, 1998, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. Surgical device for treating flat feet, comprising:
    a central cylindrical body having an outer cylindrical surface provided with a first screw thread, said cylindrical body having a head;
    an expansion cone having a longitudinally extending internal bore provided with a second screw thread mateable with the first screw thread, said cone further having an external surface of conical form; and
    an external cylinder having an internal conical surface engageable with said cone and constructed to be radially expandable in response to movement of said cone in a longitudinal direction relative to said cylinder, said cone being longitudinally moveable by rotation relative to said cylindrical body while said first and second threads are in threaded engagement with one another.

2. Device according to claim 1, wherein said cone has a small diameter end adjacent said head of said central body and a large diameter end remote from said head of said central body, and said cone cooperates with said external cylinder to expand said external cylinder in a diametrically uniform manner during longitudinal movement of said cone relative to said cylinder.

3. Device according to claim 2, wherein said cylinder has an outer lateral surface and is provided with a plurality of longitudinally extending slits which are cut in said external surface, and a plurality of longitudinally extending slits cut in the internal surface of said cylinder, said cylinder has a thickness in a direction between said external surface and said internal surface, each of said slits have a depth which is greater than ½ the thickness of said cylinder and said slits in said external surface are angularly offset from said slits in said internal surface in a manner to allow said cylinder to expand radially while undergoing an increase in diameter.

4. Device according to claim 1 wherein said cylinder is provided withdrawal prevention means comprising a plurality of ribs, each rib extending radially outwardly from said cylinder at a median angle of between 20° and 80° with respect to the longitudinal axis of said device.

5. Device according to claim 4 wherein the median angle at which each of said ribs extends is 45°.

6. Device according to claim 4, wherein each of said ribs has a height between 1 and 2 mm.

7. Device according to claim 1, wherein said cone has a distal end remote from said head of said central body and is provided with a shaped portion for engagement with a gripping device.

8. Device according to claim 7, wherein said second screw thread has a first thread direction and said shaped portion is a third screw thread formed on a distal portion of said cone and having a thread direction opposite to that of said second screw thread.

9. Device according to claim 1, wherein said central body has a distal end remote from said head and is provided at said distal end with a shaped portion for engagement by an instrument for rotating said central body.

10. Device according to claim 1, wherein said cone has a smooth external face.

11. Device according to claim 1, wherein said cone has a shaped portion for engagement with a tool to prevent rotation of said cone and permitting longitudinal movement of said cone in response to rotation of said central body relative to said cone.

12. Device according to claim 1, wherein said external cylinder is made of a deformable material.

13. Device according to claim 12, wherein said deformable material is at least one of a biocompatible material and a biodegradeable material.

14. Device according to claim 13, wherein said material is polyethylene or a metal.

15. Device according to claim 1, wherein said central body and said cone are each made of a metal.

16. Device according to claim 15, wherein each of said central body and said cone is made of titanium or stainless steel.

* * * * *